United States Patent [19]

Laughlin

[11] 4,073,833
[45] Feb. 14, 1978

[54] ENCAPSULATION PROCESS

[75] Inventor: Robert Gene Laughlin, Cincinnati, Ohio

[73] Assignee: The Procter & Gamble Company, Cincinnati, Ohio

[21] Appl. No.: 638,774

[22] Filed: Dec. 8, 1975

[51] Int. Cl.$^2$ .................. A61J 5/00; A61M 31/00
[52] U.S. Cl. .......................................... 264/4; 128/30; 128/260; 210/500 M; 252/316; 264/207; 264/233; 264/343; 424/19
[58] Field of Search .................. 264/4, 207, 200, 233, 264/343; 424/19; 252/316; 210/500 M; 128/130, 260

[56] References Cited

U.S. PATENT DOCUMENTS

| 2,246,822 | 6/1941 | Rossem | 264/343 |
|---|---|---|---|
| 2,459,927 | 1/1949 | Dreyfus et al. | 264/343 |
| 3,760,805 | 9/1973 | Higuchi | 128/260 |
| 3,760,984 | 9/1973 | Theeuwes | 128/260 |
| 3,845,770 | 11/1974 | Theeuwes et al. | 128/130 |
| 3,948,254 | 4/1976 | Zaffaroni | 128/130 |
| 3,954,925 | 5/1976 | Böddeker | 210/500 M |
| 3,991,760 | 11/1976 | Drobish et al. | 128/260 |
| 3,995,633 | 12/1976 | Gougeon | 128/260 |
| 3,995,634 | 12/1976 | Drobish | 128/260 |

OTHER PUBLICATIONS

Kirk–Othmer–Encyclopedia of Chemical Technology, "Osmosis, Osmotic Pressure and Reverse Osmosis," vol. 14, pp. 345–346, 2-1968.

Primary Examiner—Jeffery R. Thurlow
Attorney, Agent, or Firm—Jerry J. Yetter; Julius P. Filcik; Richard C. Witte

[57] ABSTRACT

An improved process for releasably enclosing a solution of a micelle-forming surfactant in a receptacle comprising a microporous cellulose membrane is provided.

8 Claims, No Drawings

ENCAPSULATION PROCESS

BACKGROUND OF THE INVENTION

Solutions of micelle-forming surfactants are releasably enclosed in receptacles comprising microporous cellulose membranes to provide controlled release articles. The membrane is initially fashioned from an acylated cellulose membrane precursor which is thereafter deacylated to cellulose using an ammonia solution. By the present invention, electrolytes are added to the ammonia solution, whereby osmotic rupture of the membrane or membrane precursor by the enclosed surfactant solution during the deacylation process is avoided.

The copending application of Robert G. Laughlin, Serial No. 560,020, filed March 19, 1975, now abandoned in favor of continuation application 714,540, filed August 16, 1976, relates to the preparation and use of controlled release articles which comprise a solution of a micelle-forming surfactant contained in a receptacle, at least one portion of the wall of said solution-containing receptacle comprising a microporous cellulose membrane. Such articles are useful, for example, in the controlled release of biologically active surfactants to provide vaginal contraceptives.

In most instances, enclosing a solution of a water-soluble material within a microporous membrane such as cellulose can lead to osmotic rupture of the membrane during exposure to an external environment having a different concentration of solute therein. In the case of the micelle-forming surfactants, however, the osmotic pressure across the membrane is relatively low due to the association of surfactant monomers into micellar structures. For this reason, stable articles comprising a microporous cellulose membrane releasably enclosing a solution of a micelle-forming surfactant can be provided.

Cellulose, itself, cannot be cast into microporous membranes for use in the foregoing type of controlled release article. Rather, cellulose is first converted into an acylated derivative, most preferably cellulose acetate, which can be suitably cast. The cellulose acetate is used in the preparation of the receptacle, to which is added the surfactant. The cellulose acetate is thereafter deacetylated with ammonia to provide the microporous cellulose membrane through which surfactant monomers diffuse in a controlled manner. (The deacetylation of cellulose acetate to cellulose with ammonia is a well-recognized organic chemical technique.)

When preparing articles of the foregoing type, it has been determined that the ammonia used to deacetylate the enclosing cellulose acetate (or, more broadly, acylated cellulose) membrane precursor somehow disrupts the micellar structure of the surfactant solution so that substantially greater amounts of free surfactant monomer are present than in the absence of ammonia. The presence of surfactant monomer in solution in the article causes a marked increase in osmotic pressure, with attendant rupture of the membrane precursor or membrane which is ultimately formed.

It has now been discovered that the addition of electrolyte to the ammonia solution used to deacetylate cellulose acetate prevents osmotic rupture of the membrane precursor or membrane. While not intending to be limited by theory, it appears that the presence of electrolyte somehow overcomes the disruptive effect of ammonia on the surfactant micelles so that substantial amounts of monomer are not formed during the deacetylation reaction. Whatever the reason, the present invention provides an improved means for preparing controlled release articles comprising a solution of micelle-forming surfactant and a microporous cellulose membrane.

SUMMARY OF THE INVENTION

The present invention encompasses an improvement in the process for releasably enclosing a micelle-forming surfactant or solution of a micelle-forming surfactant in a receptacle, wherein at least one portion of the wall of said solution-containing receptacle ultimately comprises a microporous cellulose membrane, by initially fashioning the receptacle using an acylated, preferably acetylated, cellulose membrane precursor (said receptacle containing the surfactant or surfactant solution) and thereafter deacetylating said cellulose acetate membrane precursor by contacting same with an ammonia solution, wherein said ammonia solution has dissolved therein sufficient electrolyte to avoid osmotic rupture of the membrane precursor or resulting microporous cellulose membrane.

Water-soluble primary and secondary amines can be used in place of ammonia in the process herein.

DETAILED DESCRIPTION OF THE INVENTION

The present process for fashioning controlled release articles employs conventional compounds and reactants, as described more fully hereinafter.

Cellulose acetate preferred for use as the membrane precursor material can be prepared, for example, by acetylating a cellulose feedstock using glacial acetic acid, sulfuric acid and acetic anhydride, in well-known fashion. The cellulose acetate preferred for use herein is the acetone-soluble, thermoplastic material which is commercially available from a variety of sources, and has a degree of substitution of about 2.3 acetate groups per anhydroglucose unit.

The surfactants employed in the articles prepared by the instant process are characterized by several parameters which can vary somewhat, depending on the ultimate use of the articles. In general, the surfactants are selected from those which, in combination with a microporous cellulose membrane (as described more fully in the co-pending application Ser. No. 560,020, above), provide an appropriate relationship between release and the desired end use of the article, e.g., spermicidal activity.

The surfactants herein are characterized by their ability to dissolve in a solvent (normally water) and to form an association colloid therein. The grossly anomalous (low) osmotic pressures displayed by concentrated solutions of the surfactants are attributable to the association of surfactant monomers into micellar structures. This phenomenon is of considerable practical significance in that it allows fabrication of articles containing surfactants at extraordinarily high concentrations (as compared with concentrations permitted with other, non-associative types of solutes) without osmotic rupture of the enclosing membrane. In order to realize fully the unique advantages of surfactants in this regard, it is preferred to use those surfactants having a critical micelle concentration (cmc) of at most about $1 \times 10^{-3}$ molar (M).

Various water-soluble, micelle-forming anionic, nonionic, zwitterionic, etc., surfactants well known in the detergency arts can be enclosed within articles prepared in the manner of this invention without osmotic rupture of the membrane precursor or membrane which is ultimately formed by deacetylation (or deacylation). Representative, non-limiting examples of such surfactants include: the anionics, e.g., sodium alcohol ethoxylate sulfates such as n—$C_{14}H_{29}(EO)_3SO_4^-$,$Na^+$, where EO is ethylene oxide; the nonionics, e.g., EO condensates of alcohols; and the cationics, e.g., quaternaries such as cetyltrimethylammonium bromide (CTAB).

When intended for use as between-period contraceptives or to provide other desirable effects such as the controlled release of antimicrobial surfactants, it is, of course, necessary to select surfactants which produce the desired biological response. Moreover, to secure the benefits of controlled release articles it is also necessary to select surfactants whose monomers are rapidly transported through the cellulose diffusion membrane to establish an effective concentration of surfactant in the medium external to the article.

From the foregoing considerations it will be appreciated that the desired biological response leading to the selection of a preferred surfactant can be tested in vitro in a medium (such as physiological saline, which closely approximates various body fluids) to determine the concentration at which the surfactant must be present in such medium to provide the desired response. Surfactants whose monomers are transported through the enclosing cellulose membrane of the article to provide at least the aforesaid effective concentration in the saline are useful for providing the corresponding biological response over a prolonged period of time and in a controlled manner. Over a given time period, the controlled release articles herein produce a stable maximum (or "plateau") concentration of surfactant in the external fluid. The magnitude of this plateau concentration is related to the cmc of the surfactant compound, and is approximately equal to the cmc. It follows that, for the desired effect to be realized, the ratio, R, of the cmc of the surfactant to its biologically effective concentration, $C_{biol.}$, in saline, i.e., $$R = (cmc/C_{biol.})$$

must be greater than about 1. Similar considerations hold for external media other than saline, i.e., fluid media such as body fluids, water, etc., in which the present surfactant monomers are soluble. Accordingly, the preferred surfactants for use in the articles described herein have values of R which are greater than about 1, i.e., $$R > ca. 1.$$

It will be recognized that a variety of surfactants exhibit a cmc less than about $10^{-3}$M and meet this criteria for use in the highly preferred controlled release articles prepared in the manner of this invention. Moreover, several surfactant types having the appropriate cmc provides desirable biological responses, e.g., microbiocidal or static activity and/or spermicidal activity and exhibit the requisite relationship, R > ca·1, between cmc and biological activity.

Based solely on the foregoing considerations, representative examples of preferred surfactants herein include nonionic surfactants such as $C_{10}H_{21}(OCH_2CH_2)_5OH$ (abb. $C_{10}EO_5$) and $C_{10}H_{21}(OCH_2CH_2)_6OH$ ($C_{10}EO_6$); semipolar surfactants such as $C_{12}H_{25}S(NH)_2CH_3$ and $C_{12}H_{25}(CH_3)_2AsO$; and cationic surfactants such as $C_{16}H_{33}N^+(CH_3)_3,Cl^-$ and $C_{16}H_{33}N^+C_5H_5,Cl^-$. These surfactants are characterized by R ≥ 2 and cmc < $10^{-3}$M.

It is to be understood that other useful surfactants having a cmc of $10^{-3}$M, or less, but which exhibit lower biological activity (especially as spermicidal agents), i.e., surfactants wherein ca. 1 < R < 2, can be employed in the articles prepared in the manner described herein. However, the biological response to these latter surfactants is somewhat less than that of the preferred group, and the efficacy margin, i.e., R-1, is not as great. Included among this group of surfactants are $C_{12}EO_9$; $C_{16}EO_1SO_4^-$, $Na^+$; $C_{12}(CH_3)_2PO$; $C_{10}EO_4$; $C_{12}(C_2H_5)_2PO$; $C_{16}$ ammoniopropanesulfonate; β-$OHC_{12}(CH_3)_2PO$; and nonylphenol nonaethoxylate.

As can be seen from the foregoing, various surfactant types are useful in the controlled release articles prepared in the present manner. However, when articles designed for use as between-period contraceptives are being prepared, additional physio-chemical properties of the surfactants must be considered. For example, the surfactants should be toxicologically acceptable for use in the body over extended time periods. The surfactants should also be non-irritating to the delicate tissues of the vagina and uterus. The surfactants should not substantially bind soluble proteins found in the vaginal area between periods of menstrual flow, inasmuch as the bound surfactant-protein moiety does not function as a spermicide and accelerates the depletion of surfactant from the reservoir within the article. Finally, the surfactants should be selected from those which do not bind to ionically charged sites in the enclosing diffusion membrane, since binding leads to unregulated transport through the membrane.

Based on the foregoing factors, and considering the high spermicidal activity of the compounds, the $C_{10}EO_5$ and $C_{10}EO_6$ surfactants are most preferred for use in controlled release, vaginal contraceptive articles prepared in the manner disclosed herein. As between these latter compounds, $C_{10}EO_5$ has the advantage of the lower molecular weight, and therefore provides more monomer per given weight of compound. Accordingly, $C_{10}EO_5$ is most preferred for use in the between-period, controlled release contraceptive articles prepared in the manner of this invention.

The present process is especially useful when preparing contraceptives comprising a nonionic surfactant of the foregoing type releasably enclosed by a cellulose membrane.

It will be recognized that the surfactants disclosed hereinabove are all well known from the detergency arts and can be made by various art-disclosed processes.

The articles prepared in the present manner comprise the surfactant solution and a receptacle or container therefor. At least one portion of the receptacle must ultimately comprise a microporous cellulose membrane which permits the controlled release of surfactant monomers into the environment external to the receptacle, but which prevents the transport of the larger surfactant micelles. In short, the cellulose membrane acts as a selective "sieve" at the colloidal/molecular level.

Receptacles used in the present articles can be partly made of any stable material such as glass, plastic, etc., which is not permeable, even to surfactant monomers. At least some portion of such receptacles must comprise the microporous cellulose membrane to allow controlled monomer release. Preferred articles are those wherein the receptacle comprises an envelope of the cellulose membrane.

Cellulose membranes are characterized by parameters which make them especially useful in controlled release articles of the type prepared herein. For example, cellulose is substantially water-insoluble and maintains its strength and integrity, for example, in contact with body fluids. Moreover, the toxicological and immunological acceptability of cellulose for prolonged contact with body fluids and tissues has been proven historically. Finally, cellulose membranes in the swollen state have multiple miniscule pores therethrough, i.e., are microporous. The pores of the cellulose membrane are filled, or substantially filled, with solvent (e.g., water) for the surfactant monomer. In use in the instant articles, surfactant monomers migrate from the inner reservoir of surfactant solution to the external environment by means of diffusion through the solvent in the solvent-filled pores, which pores extend from inner to outer surfaces of the articles.

As noted hereinabove, cellulose per se cannot be directly fashioned into membranes. Rather, an acylated cellulose derivative such as cellulose acetate is dissolved in a suitable solvent (e.g., acetone) together with a suitable plasticizer (e.g., triethyl citrate or diethyl phthalate) and the solution is spread onto a smooth surface, whereupon the solvent evaporates leaving a continuous film of the cellulose acetate. Having been fashioned into a suitable surfactant-containing receptacle, the film of cellulose acetate can be converted back to cellulose with an aqueous ammonia solution to provide a membrane suitable for use (in the swollen state) in the receptacle of the present articles. (Methods for casting swellable cellulose membranes are well known and form no part of this invention.)

It will be appreciated that acylated cellulosics other than cellulose acetate can be cast into films and deacylated in the present manner. For example, it is well known that cellulose propionate, cellulose butyrate, and the like, also undergo a deacylation reaction and revert to cellulose on treatment with ammonia. However, cellulose acetate is the most highly preferred acylated cellulosic in the present process, inasmuch as it is commercially available, cheap, and readily forms membrane precursors of the type used herein.

The deacylation solution used in the present process comprises ammonia dissolved in a suitable solvent, most preferably water. The aqueous ammonia solutions employed herein generally contain from about 3 to about 50%, more preferably from about 5 to about 27% by weight of ammonia, i.e., from about 1.4M to about 7.7M.

As noted hereinabove, water-soluble primary and secondary amines, especially the $C_1$–$C_5$ alkyl and hydroxyalkyl amines, can be used in place of ammonia in the present process. Aqueous solutions containing ca. 3% to 50% of such amines are useful herein. Representative amines which can be used in place of ammonia in the present process include: methylamine, diethylamine, monoethanolamine, diethanolamine, and mixtures thereof and with ammonia.

In the present process, a sufficient amount of an electrolyte (preferably sodium chloride) to avoid osmotic rupture of the membrane precursor or resulting membrane is dissolved in the ammonia (or amine) solution used in the deacylation reaction. For most purposes, the electrolyte comprises from about 3 to about 25%, more preferably from about 5 to about 15% by weight of the solution.

The electrolyte salts employed herein can be any of the well-known organic or inorganic salts which dissociate into anions and cations when dissolved in water. Such electrolytes include, for example, the alkali metal and ammonium salts of short-chain fatty acids; the alkali metal and ammonium halides; the alkali metal and ammonium nitrates; the alkali metal and ammonium sulfates; the alkali metal and ammonium carbonates; the alkali metal and ammonium bicarbonates; the short-chain tetraalkyl ammonium halides, and the like. Representative examples of such electrolyte salts include sodium chloride, potassium chloride, ammonium chloride, sodium acetate, tetramethylammonium chloride, sodium sulfate, and sodium carbonate. The alkali metal halides, especially the chlorides, are preferred for use herein inasmuch as they are relatively inexpensive and rapidly dissolve in aqueous ammonia in sufficient quantities for the present use. Sodium chloride is a highly preferred electrolyte herein.

A typical and preferred procedure for preparing a controlled release contraceptive article in the manner of the present invention is as follows. A micelleforming surfactant (preferably $C_{10}EO_5$ or $C_{10}EO_6$) is substantially enveloped within a cellulose acetate film which comprises the cellulose membrane precursor. The thickness of the cellulose acetate film is typically from about 25 microns ($\mu$) to about 75$\mu$, resulting in the formation of a cellulose membrane in a thickness (ca. 25–75$\mu$ dry; 50–150$\mu$ swollen with water) appropriate for use in a controlled release contraceptive article.

The surfactant-containing envelope is then contacted with an aqueous solution comprising from about 3% to about 50% by weight of ammonia and from about 3% to about 25% by weight of sodium chloride. For most purposes, contact times from about 5 hours to about 75 hours at temperatures of from about 25° to about 75° C suffice to substantially deacetylate the cellulose acetate membrane precursor and to form the microporous cellulose membrane therefrom, thereby providing the desired controlled release article. The precise conditions will be influenced by the membrane thickness. The thicker (75$\mu$) membranes will require longer times and higher concentrations and temperatures than the thinner (25$\mu$) membranes.

The solution of ammonia (or amine) and electrolyte which leaches into the article is removed by a water washing step after the deacetylation step. Concurrently, water flows into the article to provide a turgid, filled article containing a solution of the surfactant.

The following examples illustrate the improved process herein, but are not intended to be limiting thereof.

EXAMPLE I

Test cellulose acetate cartridges are made by cutting 1 mm. diameter, 60$\mu$ thick cellulose acetate tubing into 2 cm. lengths. One end of each tube is sealed with a droplet of cellulose acetate dissolved in acetone. When the end seal is dry, the cartridges are filled ¼ full with 100% $C_{10}EO_5$ so that when deacetylated the full cartridge will contain a 25% (wt.) $C_{10}EO_5$ surfactant solution.

Capsules prepared in the foregoing manner are deacetylated for 48 hours in 4 M (14%) ammonia solution. The capsules burst.

Capsules prepared in the foregoing manner and deacetylated in 4 M ammonia solution containing 10%

(wt.) sodium chloride were intact, and filled with solution.

Capsules prepared in the foregoing manner and deacetylated in 4 M ammonia solution containing 10% $Na_2CO_3$ and 10% $Na_2SO_4$, respectively, were intact after deacetylation; with 10% NaI, the capsules burst.

Capsules prepared in the foregoing manner and ½ full of 20% (wt.) aqueous CTAB burst on deacetylation with 4 M ammonia but remained intact when deacetylation was carried out in 4 M ammonia containing 10% (wt.) NaCl, NaI, $Na_2CO_3$ and $Na_2SO_4$, respectively. Similar results were secured with capsules containing $C_{14}H_{29}(EO)_3SO_4^-,Na^+$.

EXAMPLE II

A flat sheet of commercial cellulose acetate about 75μ thick and measuring about 7 in. × 10 in. is subjected to thermoforming methods known in the art to produce six hemispherical indentations 1 in. in diameter in the sheet. These indentations are filled to ca. 25% of their total volume with pure $C_{10}EO_5$ surfactant (using ca. 1 ml. of surfactant). A second flat sheet of the cellulose acetate film is solvent-sealed (using acetone) over the original sheet, thereby covering the indentations. The individual filled and sealed indentations are then cut from the composite sheet to provide six individual capsules which are thereafter deacetylated, as follows.

The capsules prepared in the foregoing manner are immersed in a 7.4 M (26%) aqueous ammonia solution containing 10% by weight sodium chloride dissolved therein for 96 hours at 50° C. Water passes through the membrane under the influence of osmotic forces during the deacetylation, partially filling the sealed articles. However, osmotic rupture does not occur. (A similar set of capsules containing the $C_{10}EO_5$ surfactant are immersed in 7.4 M aqueous ammonia solution, but without added electrolyte. Osmotic rupture of the capsules occurs almost immediately.)

Following the ammonia/electrolyte treatment, the articles are immersed in distilled water, whereupon they fill completely under the influence of osmosis, the entrapped air diffusing out leaving a controlled release article consisting of a microporous container of regenerated cellulose enclosing a ca. 25% solution $C_{10}EO_5$ surfactant. Ammonia and sodium chloride are removed by this water treatment.

In the process of Example I, the $C_{10}EO_5$ is replaced by an equivalent amount of $C_{10}EO_6$ and equivalent results are secured.

In the process of Example I, the pure $C_{10}EO_5$ is replaced by an equivalent amount of a 90:10 (wt.) mixture of $C_{10}EO_5$ and $C_{10}EO_6$ and equivalent results are secured.

In the process of Example I, the NaCl is replaced by an equivalent amount of KCl, NaBr, $Na_2CO_3$, $Na_2SO_4$, and $K_2CO_3$, respectively, and equivalent results are secured.

EXAMPLE III

An article especially adapted for providing controlled release of a surfactant compound into an external environment of relatively small volume and moisture content is prepared as follows.

Polyethylene tubing ca. 2 mm. diameter × 5 cm. long is dipped in a solution of cellulose acetate/acetone and withdrawn, thereby depositing a film of cellulose acetate on the tubing. The acetone solvent is allowed to evaporate, thereby solidifying the cellulose acetate on the tubing. The cylindrical cellulose acetate film (thickness of about 25μ) is thereafter removed from the polyethylene form and one end is sealed by dipping in a droplet of cellulose acetate/acetone.

The foregoing cylinder, sealed at one end, is filled to about 75% of its volume with a 50% (wt.) aqueous solution of cetyltrimethylammonium bromide (CTAB) surfactant. The open end of the cellulose acetate cylinder is sealed in the above-described manner.

The cylinder containing the CTAB solution is deacetylated using 3.7 M (13%) aqueous ammonia containing 10% sodium chloride at room temperature for 48 hours. The cylinder remains intact. Thereafter, the filled cylinder is immersed in water for several hours, allowing most of the residual ammonia and sodium chloride to diffuse into the water bath. The cylinder remains intact.

A cylinder deacetylated in the foregoing manner but without sodium chloride burst on deacetylation.

In the process of Example III, the ammonia/NaCl solution is replaced by the following deacylation solutions, respectively, and equivalent results are secured: 13% methylamine/10% NaCl; 10% diethanolamine/10% NaCl; 5% diethylamine/5% NaCl.

What is claimed is:

1. In a process for releasably enclosing an aqueous solution of a micelle-forming spermicidal nonionic surfactant in a receptacle, wherein at least one portion of a wall of said receptacle ultimately comprises a microporous cellulose membrane, by initially fashioning a receptacle containing said surfactant solution comprising an acylated cellulose membrane precursor and thereafter deacylating said membrane precursor by contacting same with an aqueous solution comprising from about 3% to about 50% by weight of ammonia or water-soluble primary or secondary amine, the improvement which comprises: dissolving sufficient electrolyte selected from alkali metal chlorides and ammonium chloride in said solution of ammonia or watersoluble amine to avoid osmotic rupture of the membrane precursor or resulting membrane.

2. A process according to claim 1 wherein the acylated cellulose membrane precursor is cellulose acetate.

3. A process according to claim 2 wherein the electrolyte is sodium chloride.

4. A process according to claim 1 wherein the electrolyte is used at a concentration of from about 3% to about 25% by weight of the ammonia solution.

5. A process according to claim 2 wherein the surfactant solution is substantially enveloped by the cellulose acetate precursor and by the resulting microporous cellulose membrane receptacle.

6. A process according to claim 5 wherein the cellulose acetate membrane precursor substantially envelops the surfactant solution and is contacted by a solution comprising from about 3% to about 50% by weight of ammonia, and from about 3% to about 25% by weight of sodium chloride, the balance comprising water, for a period of from about 5 hours to about seventy-five hours.

7. A process according to claim 6 wherein the surfactant is selected from n-$C_{10}EO_5$, n-$C_{10}EO_6$, and mixtures thereof.

8. A process according to claim 7 wherein excess ammonia and electrolyte are washed from the microporous cellulose receptacle and surfactant solution with water.

* * * * *